(12) United States Patent
Mostapha et al.

(10) Patent No.: US 11,783,485 B2
(45) Date of Patent: Oct. 10, 2023

(54) PROTOCOL-AWARE TISSUE SEGMENTATION IN MEDICAL IMAGING

(71) Applicant: Siemens Healthcare GmbH, Erlangen (DE)

(72) Inventors: Mahmoud Mostapha, Princeton, NJ (US); Boris Mailhe, Plainsboro, NJ (US); Mariappan S. Nadar, Plainsboro, NJ (US); Pascal Ceccaldi, New York, NY (US); Youngjin Yoo, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/650,311

(22) Filed: Feb. 8, 2022

(65) Prior Publication Data
US 2022/0156938 A1 May 19, 2022

Related U.S. Application Data

(62) Division of application No. 15/929,430, filed on May 1, 2020, now Pat. No. 11,288,806.
(Continued)

(51) Int. Cl.
*G06K 9/00* (2022.01)
*G06T 7/10* (2017.01)
(Continued)

(52) U.S. Cl.
CPC .............. *G06T 7/10* (2017.01); *G06N 20/00* (2019.01); *G16H 30/20* (2018.01);
(Continued)

(58) Field of Classification Search
CPC ............ G06T 7/10; G06T 2207/10088; G06T 2207/20081; G06T 2207/20084; G06T 2207/20008; G06T 7/11; G06N 20/00; G06N 3/045; G06N 3/047; G06N 3/08; G06N 3/0454; G06N 3/0472; G16H 30/20; G16H 50/20; G16H 30/40
See application file for complete search history.

(56) References Cited

U.S. PATENT DOCUMENTS 9,412,076 B2 8/2016 Sapiro et al.
11,416,653 B2 * 8/2022 Downs .................. G06N 20/00
(Continued)

OTHER PUBLICATIONS

Kendall, Alex, and Yarin Gal. "What uncertainties do we need in bayesian deep learning for computer vision?." Advances in neural information processing systems. Oct. 2017. pp. 1-12.
(Continued)

*Primary Examiner* — Xin Jia

(57) ABSTRACT

For medical imaging such as MRI, machine training is used to train a network for segmentation using both the imaging data and protocol data (e.g., meta-data). The network is trained to segment based, in part, on the configuration and/or scanner, not just the imaging data, allowing the trained network to adapt to the way each image is acquired. In one embodiment, the network architecture includes one or more blocks that receive both types of data as input and output both types of data, preserving relevant features for adaptation through at least part of the trained network.

16 Claims, 3 Drawing Sheets

Related U.S. Application Data

(60) Provisional application No. 62/907,917, filed on Sep. 30, 2019.

(51) Int. Cl.
  *G16H 30/20*  (2018.01)
  *G06N 20/00*  (2019.01)

(52) U.S. Cl.
  CPC ............... *G06T 2207/10088* (2013.01); *G06T 2207/20081* (2013.01); *G06T 2207/20084* (2013.01)

(56) References Cited

U.S. PATENT DOCUMENTS

| | | |
|---|---|---|
| 11,551,353 B2 * | 1/2023 | Golden .................. G16H 20/40 |
| 2017/0011185 A1 | 1/2017 | Schweizer |
| 2017/0116498 A1 | 4/2017 | Raveane et al. |
| 2018/0268526 A1 | 9/2018 | Mentl |
| 2020/0104674 A1 * | 4/2020 | Vellagoundar ........... G06N 3/08 |
| 2020/0175306 A1 | 6/2020 | Onoro-Rubio et al. |
| 2020/0203004 A1 | 6/2020 | Shanbhag et al. |
| 2021/0012156 A1 | 1/2021 | Vijaykeerthy et al. |
| 2021/0049743 A1 * | 2/2021 | Litwiller ............... G06T 7/0012 |
| 2021/0117729 A1 | 4/2021 | Bharti et al. |

OTHER PUBLICATIONS

Kohl, Simon, et al. "A probabilistic u-net for segmentation of ambiguous images." Advances in Neural Information Processing Systems. 2018.

Roy, Abhijit Guha, et al. "Bayesian QuickNAT: model uncertainty in deep whole-brain segmentation for structure-wise quality control." NeuroImage 195 (2019): 11-22.

* cited by examiner

PROTOCOL-AWARE TISSUE SEGMENTATION IN MEDICAL IMAGING

RELATED APPLICATIONS

The present patent document is a divisional application of U.S. patent application Ser. No. 15/929,430, filed May 1, 2020, which claims the benefit of the filing date under 35 U.S.C. § 119(e) of Provisional U.S. Patent Application Ser. No. 62/907,917, filed Sep. 30, 2019, which is hereby incorporated by reference.

BACKGROUND

The present embodiments relate to segmentation in medical imaging. In medical imaging, such as magnetic resonance (MR) imaging (MRI), various settings and scanners are available. A segmentation process optimized for a particular scanner and configuration for scanning may not operate well for other scanners and/or setting configurations. For example, MRI is used for neuro-imaging due to soft tissue contrast and the ability to sensitize the image to a variety of tissue properties (T1, T2, PD, velocity, . . . ). MR images are not typically quantitative as the image intensity depends on multiple mixed properties with a weighting that depends on the acquisition protocol setup. This lack of image standardization is a challenge for the design of automated image analytics tools such as brain tissue segmentation. Segmentation quality is impaired by poor generalization across scanners and configurations. Where the segmentation uses machine learning, sufficient data samples from a given scanner and configuration may be difficult to acquire.

To provide segmentation or other analytics that adapts to the way each image was acquired, normalization may be used. The images are projected to a common manifold, hopefully removing some of the protocol variation. Such normalization is subject to failure, especially in the presence of large structural abnormalities such as tumors or bleeds. Any normalization removes information, and that information might be relevant to diagnosis.

SUMMARY

Systems, methods, and computer readable media with instructions are provided for segmentation in medical imaging, such as segmentation for MRI. Machine training is used to train a network for segmentation using both the imaging data and protocol data (e.g., meta-data). The network is trained to segment based, in part, on the configuration and/or scanner, not just the imaging data, allowing the trained network to adapt to the way each image is acquired. In one embodiment, the network architecture includes one or more blocks that receive both types of data as input and output both types of data, preserving relevant features for adaptation through at least part of the trained network.

In a first aspect, a method is provided for segmentation by a medical imager. Protocol data is identified for a protocol used to acquire imaging data representing a patient. The imaging data is segmented with a machine-learned network. The machine-learned network outputs a segmentation in response to input of the protocol data and the imaging data. The machine-learned network includes one or more mixed blocks with learned parameters. The one or more mixed blocks are each configured to receive first protocol information and first imaging information and output second protocol information and second imaging imagining information. An image representing the segmentation is displayed.

In one embodiment, the protocol data includes an MR weighting type. The protocol data may include a setting for a sequence parameter, geometrical information of a scan of the patient, and/or task specific information. The protocol information is the protocol data or a feature derived from the protocol data (e.g., feature from a previous network layer).

In an embodiment, the machine-learned network is a U-net including the one or more mixed blocks at a layer other than an input or an output of the U-net. For example, the mixed block is configured to receive the first protocol information as multiple protocol features output by a previous layer of the machine-learned network, and the mixed block is configured to receive the first imaging data as multiple imaging features output by the previous layer of the machine-learned network. Alternatively or additionally, the input layer of the machine-learned network has the mixed block, so the first protocol information is the protocol data and the first imaging information is the imaging data.

In another embodiment, the machine-learned network is a U-net with a conditional network including the one or more mixed blocks. The conditional network outputs to a bottleneck of the U-net.

In an embodiment, the mixed block includes a normalization layer, a linear layer, and a non-linear layer. For example, the mixed block includes: (1) a first normalization configured to output statistical information from the input imaging information to concatenate with the first protocol information and output normalized imaging information, (2) a first fully connected layer configured to output a scale value to invert the normalized imaging information, (3) a batch normalization receiving the concatenated first protocol information and the statistical information, (4) a second fully connected layer configured to receive an output of the batch normalization and output to a summer and a first non-linear activation function, (5) the first non-linear activation function configured to output the second protocol information, (6) a multiplier configured to invert the normalized imaging information based on the scale value, (7) a convolution layer configured to convolve with the inverted, normalized imaging information, (8) the summer configured to sum an output of the convolution layer with the output of the second fully connected layer, and (9) a second non-linear activation function configured to output the second imaging information in response to input of an output from the summer. Other arrangements may be used, such as the mixed block including an instance normalization configured to output a skewness and/or kurtosis concatenated with the protocol information.

For training, the loss is based on the segmentation. Multi-task training may be used, such as a loss based on the segmentation and uncertainty estimation.

In a second aspect, a method is provided for segmentation by a magnetic resonance imager. Both protocol and image data are input to a machine-learned network. The machine-learned network was trained with layers having both input and output couples related to both the protocol and the image data. Locations are output by the machine-learned network in response to the input of both the protocol and image data, and a magnetic resonance image showing the locations is displayed. For example, the image data represents a brain of a patient. The displayed magnetic resonance image is of the brain.

In one embodiment, the layers with the couples include image features separated by type of tissue. Various layer configurations may be used, such as each of the layers having both input and output couples includes normalization, linear, and non-linear portions. The output is based on the normalization, linear, and non-linear portions.

The use of both protocol and imaging data, such as the input and output couples in the layer or layers, allows the machine-learned network to operate well for different protocols used on different patients by different scanners.

In a third aspect, a system is provided for segmentation of brain tissue in magnetic resonance imaging (MRI). An MRI scanner is configured to scan the brain tissue of a patient. The scan provides scan data and meta data. The meta data represent the scan, and the scan data representing the patient. An image processor is configured to segment between different types of the brain tissue by application of the scan data and the meta data to a machine-learned model. The machine-learned model outputs the segmentation. A display is configured to display the segmentation of the brain tissue.

In one embodiment, the machine-learned model is a neural network with a block having input channels for first features related to the meta data and for first features related to the scan data and having output channels for second features related to the meta data and for second features related to the scan data. For example, the block is configured to pass information from the first features related to the meta data to a path from the input of the first features related to the scan data to the output of the second features related to the scan data. In another example, the block includes normalization, linear, and non-linearity layers.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Protocol-aware segmentation uses multimodal deep learning. For example, MR brain tissue segmentation leverages available sequence parameters to learn to adapt to acquisition variations. Since the MR signal is controlled by the acquisition protocol, the MR signal or imaging data may be described by the values given to the parameters adjustable by the technologist (e.g. TR, TE, flip angle, preparation pulses, . . . ). The MR tissue segmentation is machine learned from a couple (image, meta-data) to a target segmentation mask. The scan meta-data are not images themselves, so an ad-hoc network architecture is used to accept the scan meta-data as a network input. For example, the deep network is a combination of mixed blocks that all have a couple (meta-data, images) as inputs and outputs. The mixed blocks are a generalization of the convolutional or fully connected deep learning blocks, such as made of a normalization layer, a linear layer and a nonlinearity.

The segmentation is formulated as a function of the acquired images and the way the images were acquired instead of the images alone. As a result, different systems can be proposed at the scanner and in stand-alone post-processing applications. The same segmentation may be applied regardless of scan configuration and scanner. The mixed network architecture jointly processes image and scalar data, so is flexible.

Figure 1:
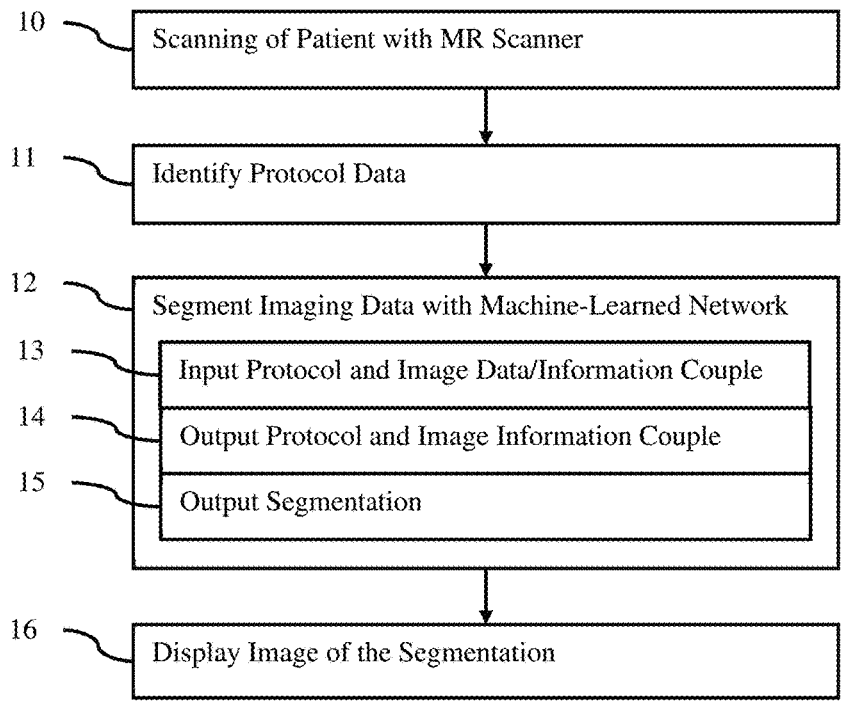
FIG. 1 is a flow chart of one embodiment of a method for segmentation by a medical imager.

FIG. 1 shows one embodiment of a method for segmentation by a medical imager, such as segmentation by an MR imager. The segmentation is provided by a machine-learned model, which operates on both imaging data and meta-data. For example, the machine-learned model includes one or more blocks that receive both types of data as input and output features for both types of data.

The method is implemented by an imager (e.g., MR scanner) to scan a patient in act 10. An image processor, such as part of the MR scanner, server, computer, or workstation, performs acts 11-15. The image processor, using a display screen, displays the image in act 16. Other devices may be used.

The method is performed in the order shown (top to bottom or numerical). Other orders may be used. For example, act 11 is performed before act 10.

Additional, different, or fewer acts may be provided. For example, acts 10, 13, and/or 14 are not provided. As another example, acts for positioning the patient, configuring the imager, and/or assisting user diagnosis, tracing, and/or treatment planning are provided.

The examples used herein are for MRI of the brain. In other embodiments, other tissue, organs, anatomy, or regions of the patient are scanned. In yet other embodiments, other types of imagers are used instead of MR, such as a computed tomography or ultrasound imager.

In act 10, the MR scanner scans a patient. The patient is positioned in the bore of the MR scanner and subjected to the $B_0$ main magnetic field. MR pulses are transmitted in sequence with gradient magnetic fields. The responses are measured as k-space data. The scan data are measurements (e.g., k-space data or data reconstructed from the k-space data (e.g., reconstructed object domain)).

The scan is a volume scan, such as measuring for locations distributed along three dimensions. In alternative embodiments, a planar scan is performed.

The scan is of the brain of a patient. Alternatively, the scan is of the liver or other organ of the patient. The scan may be of the entire organ, multiple organs, and/or part of one or more organs. Brain tissue and brain tumor tissue examples are used herein, but other tissues and/or tumors may be scanned.

The scan is performed using a particular imager or type of imager (e.g., manufacturer and model) configured pursuant to a scan protocol. The user configures the imager. Alternatively, automated or default configuration is provided.

Different scan patterns, including different pulse arrangements, may be used to acquire data representing any one or more different metrics. The different metrics include structural parameters, diffusion parameters, and/or spectroscopy parameters. Structural measurements measure the response from anatomy or tissue. Any of various structural measurements may be used. Example parameters include T1, T2, FLAIR, and T1 Post-Contrast measurements. Diffusion measurements measure the response of fluid as a spatial distribution (how much water and/or distribution of water in a tissue) or a directional component of water distribution. Example diffusion measurements include diffusion tensor imaging (DTI), such as DTI axial diffusivity, DTI fractional anisotropy, and DTI mean diffusivity. Another example is diffusion weighted imaging (DWI), such as DWI $B_0$ measurements. Spectroscopy measurements measure response by particular molecules. Example spectroscopy measurements include N-acetyl aspartate (NAA), creatine, lactate, water, gix, inositol (e.g., myo-Inositol), glycine, acetate, alanine, glutamate, succinate, and choline measurements. Other categories of MRI parameters may be used. For example, functional MR imaging may be used, such as measuring the uptake or operation of a body process. MR perfusion measurements using contrast-enhanced methods (DCE or DSC) may be used.

For a given weighting type or type of MR measurement, various free parameters may be set (i.e., values assigned or adjusted by a technologist). Some example settings for configuring the scan include repetition time (TR), time-to-echo (TE), flip angle, and preparation pulses. The configuration settings are meta-data, and include sequence parameters (e.g., TR, TE, TI, flip angel, field strength, acquisition plane), geometrical image information (e.g., resolution, field of view), scanner information (e.g., manufacturer, scanner model, coil type), and/or prior intensity statistics of each tissue type (e.g., mean intensity of different types of tissue (e.g., white matter, gray matter, and cerebral spinal fluid)). Any of this meta-data may be protocol data where the protocol is the arrangement used for scanning a patient for a particular purpose.

The scan configuration may result in given field of view, density, voxel or pixel size, or other information. The scanner may have selectable hardware as part of the scan configuration. The scan configuration and/or scanner may result in imaging data having particular characteristics, such as noise level. The scan configuration may be associated with patient information, such as patient demographics. The characteristics of the scan, scanner, and/or patient are provided as meta-data or protocol data.

In act 11, the image processor identifies protocol data for a protocol used to acquire imaging data representing a patient. The image processor identifies by loading, mining, searching for, and/or receiving configuration information for the scan of the patient. For example, the imaging data is stored using the DICOM format. The protocol data is stored in DICOM tags (e.g., headers). As another example, the scanner logs the configuration information, so the image processor looks-up the configuration. In yet another example, a value or values for the scanner and/or tissue are known or recorded, such as the noise level for the scanner. In another example, demographics or other scan settings for the patient are look-up from a patient computerized medical record.

The value or values of one or more settings are identified. Rather than determining all of the protocol data, the value or values for a sub-set of one or more characteristics of the protocol for scanning the patient are found. For example, the MR weighting type is identified. In another example, the value or values for a sequence parameter, geometrical information of a scan of the patient, and/or task specific information are identified. Example sequence parameters are TR, TE, T1, and/or flip angle. Example geometrical information are resolution and/or field of view. Example task-specific information are tissue intensity means.

In act 12, the image processor segments the imaging data. The imaging data is scan data in the object domain, such as after reconstruction or transformation from k-space. The imaging data may be scan data to be used to generate a spatial representation of the patient and/or may be data in an image format, such as data of a previously displayed image. The imaging data is in a scan format or a display format. The imaging data may represent different locations in the patient, such as pixel locations in a plane or voxel locations in a volume.

The segmentation identifies a sub-set of the locations represented by the imaging data. The locations are associated with particular anatomy (e.g., tissue), object, organ, lesion, tumor, cyst, or device. For example in brain MRI, the segmentation identifies locations of white matter, gray matter, or cerebral spinal fluid (CSF). The segmentation may indicate the locations associated with each of the three different types of tissue in the brain. One segmentation may label locations for multiple tissues. Alternatively, different segmentations are performed for different tissues. In one embodiment, a skull stripping segmentation identifies skull locations to be removed, and another segmentation is used for normal tissue segmentation. Hierarchal or separate models may be used for identifying locations of the different types of normal tissue and/or other objects.

The segmentation is performed with a machine-learned model, such as a machine-learned neural network. The machine-learned model may be any now known or later develop machine-trained model, such as a Bayesian network or a support vector machine. In one embodiment, the machine-learned model is a neural network trained with deep learning.

Acts 13 and 14 are for application of the machine-learned model, where data is input to the model, which generates output. For adapting to different configurations and/or scanners, the input of act 13 to the machine-learned network includes both protocol and image data. The machine-learned network uses the protocol data to segment the image data, allowing for the same network as trained with a segmentation loss to segment for different protocols used on different patients with different scanners. The machine-learned network outputs the segmentation in act 15 in response to the input of act 13. The output of act 14 may be within the network, such as one layer outputting both protocol and image information as a couple. The machine-learned network is trained with one or more layers having both input and output couples related to both the protocol and the image data. In training, the segmentation loss is used to learn values for parameters along separate protocol and imaging paths. The one loss learns values for both types of information within the network.

The machine-learned network is a fully connected, convolutional, or another neural network. Any network structure may be used. Any number of layers, nodes within layers, types of nodes (activations), types of layers, interconnections, learnable parameters, and/or other network architectures may be used. Machine training uses the defined architecture, training data, and optimization to learn values of the learnable parameters of the architecture based on the samples and ground truth of training data.

For training the model to be applied as a machine-learned model, training data is acquired and stored in a database or memory. The training data is acquired by aggregation, mining, loading from a publicly or privately formed collection, transfer, and/or access. Ten, hundreds, or thousands of samples of training data are acquired. The samples are from scans of different patients and/or phantoms. Simulation may be used to form the training data. The training data includes the desired output (ground truth), such as segmentation, and the input, such as protocol data and imaging data.

A machine (e.g., image processor, server, workstation, or computer) machine trains the neural network to segment. The training uses the training data to learn values for the learnable parameters of the network. The training determines the values of the learnable parameters of the network that most consistently output close to or at the ground truth given the input sample. In training, the loss function is the cross entropy between prediction segmentation and ground truth segmentation. Other loss functions, such as L1 or L2, may be used. Adam or another function is used for optimization.

The loss function in training compares the estimated segmentation to a ground truth segmentation. In other embodiments, multi-task training is used. For example, the network is trained with multi-task training using uncertainty estimation. Model uncertainty is quantified based on Dice agreement in Monte Carlo samples from dropout network's outputs. Other uncertainty measures may be used including coefficient of variation (CV,) Jaccard coefficient (IOU), or mean entropy. The network is trained to simultaneously minimize segmentation and uncertainty loss (multitask loss). Data (aleatoric) uncertainty captures noise inherent in the observations, and model (epistemic) uncertainty accounts for uncertainty in the model. Either or both types of uncertainty may be used for the multitask loss. For example, a Bayesian deep learning framework combines input-dependent aleatoric uncertainty and epistemic uncertainty. The variance of the output is also predicted by the model in addition to the output for aleatoric uncertainty while marginalizing the parameters for epistemic uncertainty. For classification tasks including segmentation, sampling is from the logits, which is a fraction of the network's compute. This objective may be interpreted as learning loss attenuation. The hyperparameter optimization for uncertainty modeling may be improved by adjustment to dropout rate, number of Monte Carlo samples needed, learning rate, weights regularization, and/or alternative network designs.

Once trained, the machine-learned or trained neural network is stored for later application. The training determines the values of the learnable parameters of the network. The network architecture, values of non-learnable parameters, and values of the learnable parameters are stored as the machine-learned network. Copies may be distributed, such as to MR scanners, for application. Once stored, the machine-learned network may be fixed. The same machine-learned network may be applied to different patients, different scanners, and/or with different imaging protocols for the scanning.

The machine-learned network may be updated. As additional training data is acquired, such as through application of the network for patients and corrections by experts to that output, the additional training data may be used to re-train or update the training.

The machine-learned network, as trained, has an architecture designed for accepting protocol data. A layer, group of nodes, or other internal part of the network includes one or more mixed blocks with learned parameters. Each mixed block is configured to receive protocol information and imaging information and output further protocol information and further imaging information. Both input and output couples of both types of information are provided for the block or blocks. The imaging features include features of spatial representations. The protocol features include features of scalar or continuous values. In one embodiment, an MR tissue segmentation is learned as a function from an input couple (image, meta-data) to a target segmentation mask. The scan meta-data are not images themselves, therefore an ad-hoc network architecture is used to accept this protocol data as a network input.

Where the block is an initial or input layer of the machine-learned network, the protocol data identified in act 11 and the imaging data from the scan of act 10 are input. Where the block is not at the input, protocol features derived from the protocol data and imaging data features derived from the imaging data are input. Alternatively, a skip connection is provided to input the initial imaging and/or protocol data. Any number of features for protocol information and/or imaging information may be input and/or output. For example, an initial layer of the network is formed from a mixed block, so receives the imaging data and protocol data. This initial layer identifies values for multiple protocol features and multiple imaging features. The values for the multiple features are output from this initial block to a subsequent mixed block, which receives in corresponding channels the values for the protocol features derived from the protocol information by the initial mixed block. The subsequent mixed block also receives in corresponding channels the output values for the imaging features derived from the imaging information by the initial mixed block. Both types of information are propagated through at least part of the network, with each stage (e.g., layer) deriving further features.

Figure 2:
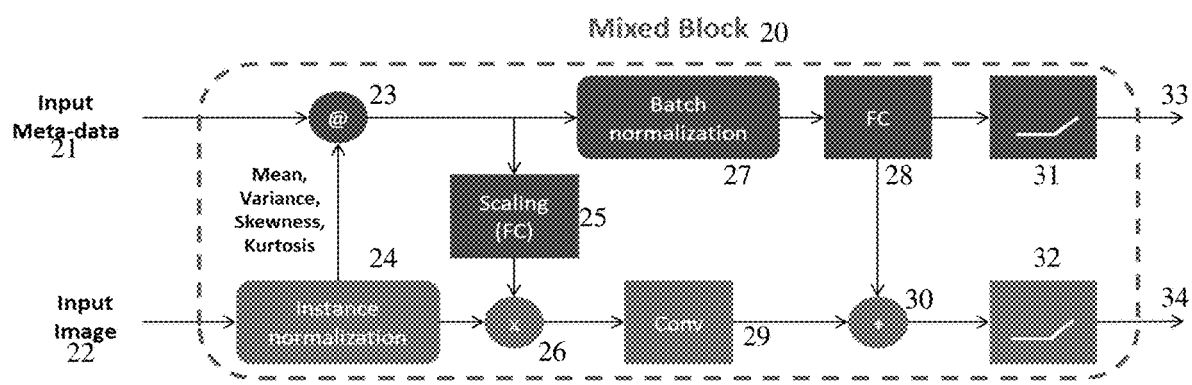
FIG. 2 illustrations one embodiment of an architecture of a mixed block used for segmentation.

The mixed block is a generalization of the convolutional or fully connected deep learning blocks. In one embodiment, the block is configured as a normalization part, a linear part and a nonlinear part. The mixed block includes functions, nodes, or operations appropriate both types of data. FIG. 2 shows one example mixed block 20 using a normalization part (e.g., instance normalization 24), a linear part (e.g., fully connected layers 25 and/or 28), and nonlinear part (e.g., nonlinear function layers 31 and/or 32). Additional, different, or fewer parts may be included.

The instance normalization 24 receives the image data or information 22 as an input. The instance normalization 24 includes none, one, or some learnable parameters. A normalization of each input channel (e.g., each input image or feature) is performed, such as normalization based on mean and variance. The output is normalized image data for each feature channel. Another output is statistical information, such as the mean and variance. In one embodiment, other statistical information is calculated, such as skewness and/or kurtosis.

The statistical information is treated as further protocol information, so concatenated with the input protocol information. The instance normalization is used on the image data both as a normalization layer and as an embedding layer: on top of the normalized image data, the layer also concatenates the computed channel means and variances with or without higher-order statistics (e.g., skewness and kurtosis) to the meta-data.

The input protocol information (e.g., meta-data 21) with or without the statistics from the instance normalization 24 are input to the scaling layer 25 and a batch normalization layer 27. The scaling layer 25 is a fully connected layer configured to determine one or more scales. The scaling layer 25 includes one or more learnable parameters. A scale is provided for each channel of the instance normalization 24, such as a scale value or scale field for each feature output by the instance normalization.

The scaling layer 25 outputs a scale or scales to be multiplied 26 with a feature or features output by the instance normalization. This multiplicative connection 26 from the protocol path to the image path is provided to invert the divisive normalization by an instance norm.

The output of the multiplication is to a convolution layer 29. The convolution layer 29 includes one or more learnable kernels for filtering the imaging information.

The batch normalization 27 receives the concatenated protocol information and statistical information. The batch normalization layer 27 includes learnable parameters. The batch normalization layer 27 outputs protocol information to a fully connected layer 28.

The fully connected layer 28 outputs values to be added to an output of the convolution layer 29. The fully connected layer 28 includes learnable parameters. This addition by the adder 30 expands and concatenates the protocol information to the image information. The values for adding are processed as scalars.

In the path for protocol information, a non-linear activation function 31 is provided. The function 31 may include one or more learnable parameters. This function maps the protocol information, resulting in the output of one or more features representing derived protocol information 33.

In the path for the imaging information, a non-linear activation function 32 is provided. The function 32 may include one or more learnable parameters. This function maps the imaging information, resulting in the output of one or more features representing derived imaging information 34.

The mixed block 20 provides two paths, one for protocol information and one for imaging information. These two paths provide for input of both protocol and imaging information as well as output of both derived protocol and derived imaging information. The paths are linked by one or more connections, such as the imaging information path providing statistical information to the protocol path and the protocol path providing scaling or other values to the imaging path. Other arrangements with fewer, additional, or different connections may be provided.

In one embodiment, the imaging path includes different features for different tissues. The protocol information does or does not also include protocol information for different features, such as including concatenated statistical information for different types of tissue. The image features are separated by the type of tissue, such as providing one or more imaging features for each type of tissue. In the brain imaging example, the mean intensity by tissue type is concatenated 23. The mean intensity may be estimated using Gaussian mixture model or another estimator.

The mixed block or blocks 20 may be used in any network architecture. Any part (e.g., layer) of a neural network may be formed by a mixed block. Once the base mixed block 20 is defined, the combination methods of deep learning may be extended to be a deep mixed network. For MR image segmentation, a two or three-dimensional (3D) U-NET or conditional U-NET architecture may be created to jointly learn from the input scan in addition to meta-data (e.g., sequence parameters such as TR, TE, TI, flip angel, field strength, and acquisition plane, geometrical image information such as resolution and field of view, scanner information such as manufacturer, scanner model, and coil type, and prior intensity statistics of each tissue type such as mean intensity of WM, GM, CSF). Other image-to-image networks, such as encoder-decoder arrangements or variational auto encoders, may be used instead of or as part of the U-Net.

Figure 3:
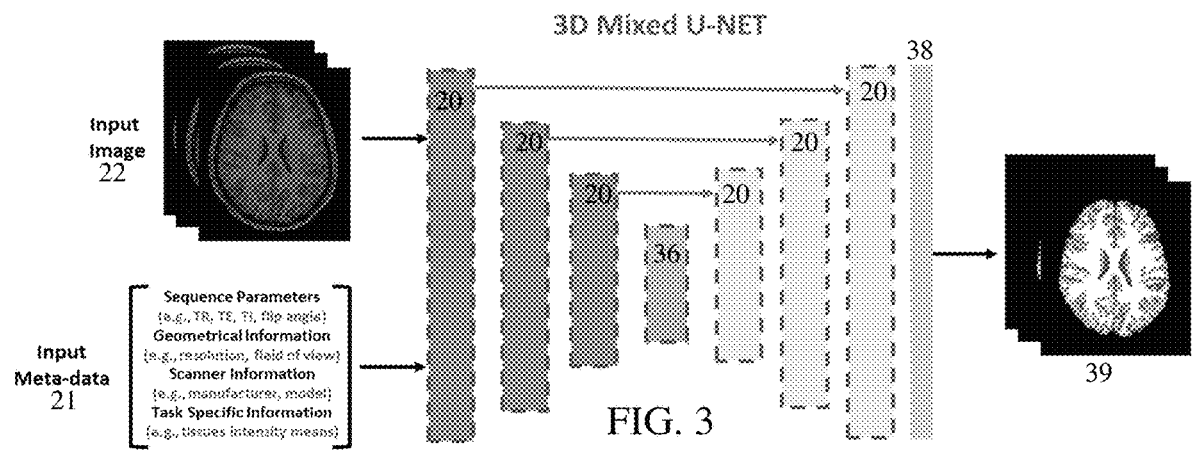
FIGS. 3 and 4 illustrate example U-Nets using mixed blocks for machine-learned model-based segmentation.

FIG. 3 shows a U-net architecture. The input image data 22 and protocol information 21 are provided to an initial layer of an encoder. The encoder is formed from one or more layers of mixed blocks 20. The encoder feeds features to a bottleneck layer 36, which outputs to the decoder formed of one or more layers of mixed blocks 20. A final layer 38, such as a softmax (classification) layer of the decoder generates the segmentation output (e.g., map of locations) from features from the previous layer. Skip connections may be provided as shown in FIG. 3, but networks without skip connections may be used. In the example of FIG. 3, all the layers of the encoder are formed from mixed blocks 20 and the non-output layers of the decoder are formed from mixed blocks 20. The bottleneck 36 may be a mixed block 20. Any of the layers may be formed from other structures than the mixed block 20. There may be only one mixed block 20 used. The mixed block 20 may be used for the initial layer, for layers other than the input or output layers, and/or both.

Figure 4:
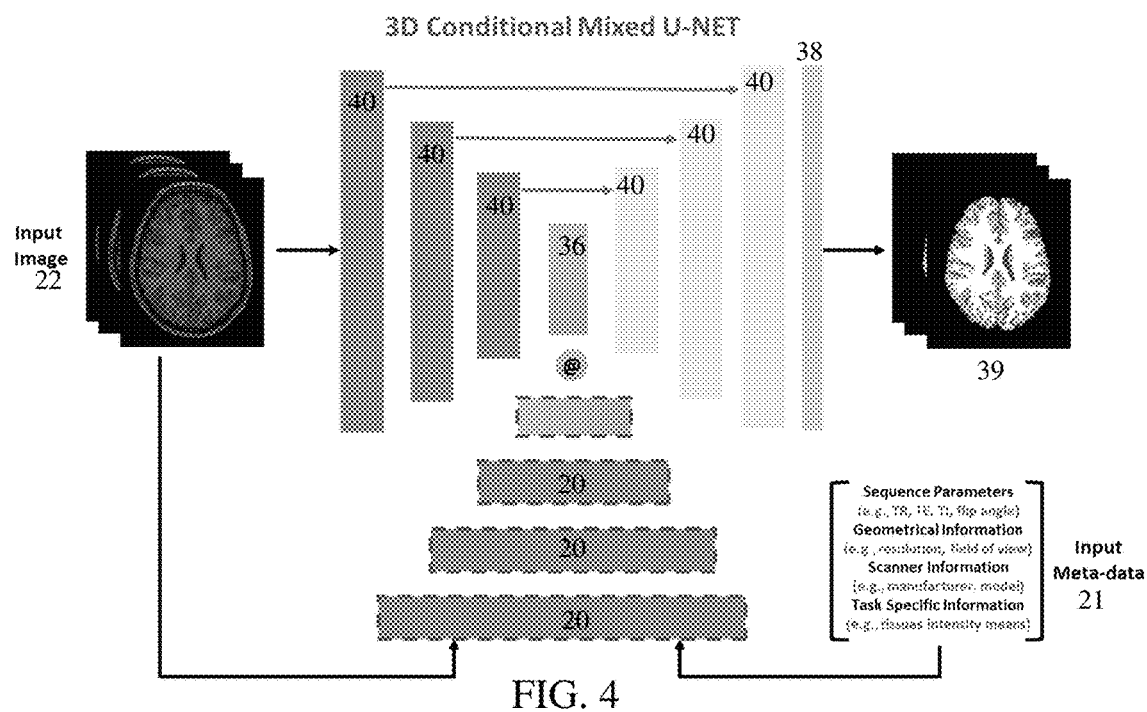

FIG. 4 shows another example network architecture. A conditional U-net is provided. The U-net, including the encoder and decoder, are formed from neural network layers 40, which layers 40 may or may not be mixed blocks. For example, the layers 40 are convolutional blocks or layers. An additional encoder is formed from mixed blocks 20 to receive both imaging data 22 and protocol data 21. The features output by this network are provided to the bottleneck 36 of the U-net. At least one of the layers for the network outside of the U-net include the mixed block 20 for feeding information responsive to both imaging and protocol information to the bottleneck 36.

In other embodiments, a dense U-net uses one or more mixed blocks. For example, one or more layers of the encoder and/or decoder are densely connected layers where information from multiple previous blocks of the layer feeds to an output for the layer. The mixed block 20 may be used in the architecture for these dense layers, such as forming densely connected mixed blocks as the layer of the U-Net.

Other types of embedding layers (e.g., instance normalization 24) beyond the utilized high-order statistics (e.g., quantiles, covariance) may be used. Only one, a sub-set, fewer than all or all of the blocks or layers in the U-net may use mixed blocks. For less than all, different depths in the encoder and/or decoder use both the protocol (e.g., metadata) and imaging paths, and other depths or layers output features in one or more channels without the protocol and imaging data separation. The ordering of the normalization, linear, and nonlinear parts of the mixed block 20 may be changed, such as providing an initial nonlinear part before normalization or the linear parts. Embedding layers are used to feed the images back to the protocol information. Robustness may be improved by extending the U-Net architecture with mixed blocks to a probabilistic version.

For application of a previously trained machine-learned network or other model, the previously unseen imaging and protocol data is input for the segmentation of act 12. The protocol and image data or information derived from the data is input to one or more mixed blocks 20 in act 13. These mixed blocks 20 output protocol information and imaging information in act 14. The machine-learned network, using the input and output of acts 13 and 14, outputs a segmentation in act 15.

In act 15, the image processor outputs locations identified by the machine-learned network in response to the input of both the protocol and image data. The segmentation, such as identification of locations of one or more types of tissue, is output. Due to operation of the mixed block or blocks, such as including the normalization, linear, and non-linear portions, the segmentation may be responsive to or account for differences in the scan configuration, patient, scanner used, and/or prior intensity statistics.

In act 16, the image processor generates an image based on the output segmentation. The image is displayed on a display screen or device. The image represents the patient without the tissue identified in the segmentation, with just the tissue identified in the segmentation, or with the segmented tissue highlighted relative to other tissue. The image shows locations of anatomy or response to the scanning, with some of the intensities for locations identified in segmentation as altered or displayed differently than intensities for other locations. The image represents the segmentation.

Where voxels are segmented, the image may be a two-dimensional or planar slice of the volume. Alternatively, three-dimensional rendering (e.g., volume rendering) is performed to provide a two-dimensional image for display based on the 3D segmentation.

The image may include other information. For example, the segmentation by class is used to generate a graphic or highlighting. An image from one or more of the MR parameters is generated. The graphics or highlighting from the classification is applied or overlaid on the MRI image. Alternatively, the segmentation is displayed without being an overlay.

In one embodiment, the image is an MR image showing or representing the patient, such as an MR image of the brain. One or more types of tissues, lesion, or other structure in or part of the brain of the patient is shown separately or highlighted based on the segmentation.

Performance of the machine-learned classifier may be tested. In one embodiment, training data is available for 896 scans with two types of weighting (T1w and T2w). The ground truth segmentation is provided as part of the FMRIB software library (FSL), created with pseudo GT. Tissue segmentation as ground truth uses the FSL. An imbalanced training is used to simulate a challenging task. For T1w, 50% are used to train, 25% are used to validate, and 25% are used to test. For T2w, 10% are used to train, 25% are used to validate, and 25% are used to test. The protocol data is a binary label for MR weighting type (i.e., T1w vs. T2w). The 3D U-Net architecture of FIG. 3 is used in general with or without mixed blocks 20.

To establish a baseline, the 3D U-Net architecture is trained on T1w only or T2w without meta-data, and the 3D U-Net architecture is trained on both T1w and T2w without meta-data. In another baseline, the 3D U-Net architecture is trained on T1w and T2w with meta-data added using an auxiliary network in a multi-task learning framework. The auxiliary separately receives the meta-data to estimate meta-data, so the meta-data is related to the imaging data through the multi-task learning rather than including both types of data as input to the same network with interconnections between the types within the network. In approaches using mixed blocks, the 3D U-Net architecture (i.e., mixed 3D U-Net) is trained on T1w and T2w with the meta-data, the 3D U-Net architecture of FIG. 3 with dense connections in each layer is trained on T1w and T2w with the meta-data, and the 3D conditional U-Net architecture (see FIG. 4) is trained on T1w and T2w with the meta data. In the embodiments using mixed blocks, each layer including the bottleneck is formed from a mixed block. Table 1 below shows the segmentation performance results for these seven machine-learned networks.

TABLE 1

| Train | Test | CSF Dice Score | GM Dice Score | WM Dice Score |
|---|---|---|---|---|
| T1w | T1w | 0.8642 | 0.9048 | 0.929 |
| (U-Net) | T2w | 0.0616 | 0.7801 | 0.0012 |
| T2w | T1w | 0.1737 | 0.6714 | 0.0003 |
| (U-Net) | T2w | 0.815 | 0.8749 | 0.9126 |
| T1w, T2w & Meta data | T1w & Meta-data | 0.8656 | 0.9148 | 0.9430 |
| (U-Net + Auxiliary Net) | T2w & Meta-data | 0.7873 | 0.8620 | 0.9170 |
| T1w, T2w & Meta-data | T1w & Meta-data | 0.9198 | 0.9465 | 0.9640 |
| (Mixed U-Net) | T2w & Meta-data | 0.8395 | 0.8975 | 0.9411 |
| T1w, T2w & Meta data | T1w & Meta-data | 0.8741 | 0.9248 | 0.9497 |
| (Mixed Dense-U-Net) | T2w & Meta-data | 0.7725 | 0.8414 | 0.9041 |
| T1w, T2w & Meta-data | T1w & Meta-data | 0.9009 | 0.9304 | 0.9480 |
| (Mixed Conditional-U-Net) | T2w & Meta-data | 0.8274 | 0.8850 | 0.9203 |

The machine-learned network of FIG. 3 shows the best CSF, GM, and WM Dice scores. The U-Nets using mixed blocks as trained show scores that provide similar or better accuracy despite being applicable to different types of scans and corresponding imaging data.

In another test, 16,462 T1w images with meta-data and tissue segmentation using FSL are available from the ANDI dataset. 50% are used to train, 25% are used to validate, and 25% are used to test. The meta-data used as input has values for pulse sequence, coil, acquisition plane, manufacturer of scanner, manufacture model of scanner, field strength, TE, TR, TI, flip angle, field of view, and voxel size. For a baseline, the 3D U-Net architecture is trained on the T1w images without meta-data and trained on the T1w images with meta-data used in the auxiliary network with multi-task learning. For use of the mixed blocks, the 3D U-Net architecture of FIG. 3 (mixed blocks 20 being used for every layer including bottle neck 36 and excluding output layer 38) and the 3D conditional U-Net architecture of FIG. 4 (mixed blocks 20 being only used in the additional encoder network with convolutional blocks being used for the encoder and generator of the U-Net) are trained on the T1w with the meta-data. Table 2 shows the results.

TABLE 2

| Train | Test | CSF Dice Score | GM Dice Score | WM Dice Score |
|---|---|---|---|---|
| T1w & Meta-data (U-Net) | T1w | 0.867 | 0.869 | 0.886 |
| T1w & Meta-data (U-Net + Auxiliary Net) | T1w & Meta-data | 0.870 | 0.875 | 0.890 |
| T1w & Meta-data (Mixed U-Net) | T1w & Meta-data | 0.885 | 0.895 | 0.898 |
| T1w & Meta-data (Mixed Conditional U-Net) | T1w & Meta-data | 0.850 | 0.853 | 0.868 |

The machine-learned network of FIG. 3 with mixed blocks provides the best scores.

Figure 5:
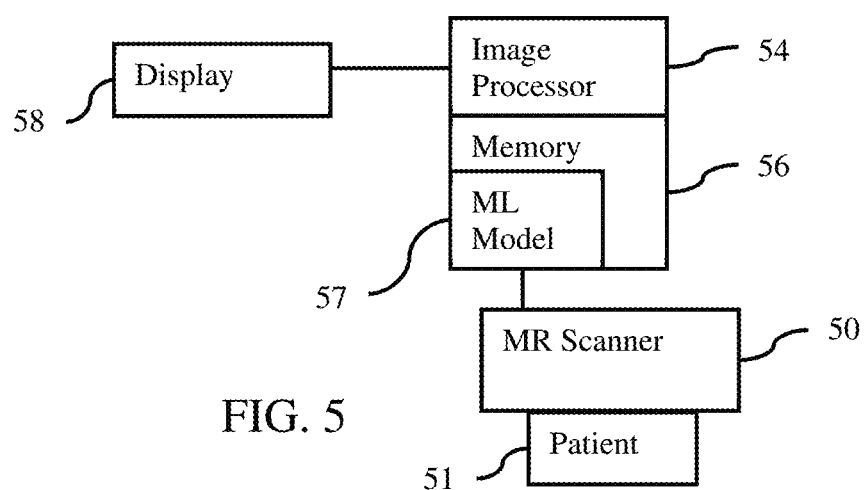
FIG. 5 is a block diagram of one embodiment of a system for segmentation in MRI.

FIG. 5 is a block diagram of a medical imaging system for segmentation in MRI, such as segmentation in brain tissue. The system is for application of a machine-learned model 57 and/or for training of the machine-learned model 57. The machine-learned model operates on input of both protocol data and image data to segment, such as including one or more mixed blocks.

The medical imaging system includes the display 58, memory 56, and image processor 54. The display 58, image processor 54, and memory 56 may be part of the MR scanner 50, a computer, server, or another system for image processing to segment. A workstation or computer without the MR scanner 50 may be used as the medical imaging system. Additional, different, or fewer components may be provided, such as including a computer network for communication. In other embodiments, the system is for use in computed tomography, ultrasound, or other types of medical imaging, so provides a corresponding type of scanner 50 and segmentation using meta-data.

The MR scanner 50 is a medical diagnostic imaging system configured to scan a volume of a patient for each of multiple MR parameters. A main magnet or coil generates a substantially uniform magnetic field through the patient 51. Gradient coils, local coils, and/or a whole-body coil generate a pulse sequence to shift spin axes of molecules in the patient away from the uniform magnetic field lines. The local coils and/or whole-body coil detect radio frequency emissions caused by the relaxation of the spin axes of the molecules returning to the magnetic field lines. This k-space data is reconstructed into an object or spatial domain using Fourier processing. After transform, the scan or image data represents tissue response from a region of the patient 51.

Different pulse sequences are performed for different of the MRI parameters. The MR scanner 50 is configured, by settings, to scan the tissue of the patient. For example, a user selects an application for brain tissue or brain tumor scanning. The MR scanner 50 is configured to perform measurements for any number of different parameters or types of MR scans with any number of configurations for each of the different types. The settings are used as meta-data or protocol data. Characteristics of the MR scanner 50 or the scan of the patient, such as noise level, may be included or used as the meta-data or protocol data.

The image processor 54 is a control processor, general processor, digital signal processor, three-dimensional data processor, graphics processing unit, application specific integrated circuit, field programmable gate array, artificial intelligence processor, digital circuit, analog circuit, combinations thereof, or another now known or later developed device for segmenting or classifying. The image processor 54 is a single device, a plurality of devices, or a network. For more than one device, parallel or sequential division of processing may be used. Different devices making up the image processor 54 may perform different functions. In one embodiment, the image processor 54 is a control processor or other processor of a medical diagnostic imaging system, such as the MR scanner 50. The image processor 54 operates pursuant to stored instructions, hardware, and/or firmware to perform various acts described herein, such as registering, locating, classifying, and generating of the confidence map.

The image processor 54 is configured to segment between different types of the brain or other tissue by application of the scan data and the meta data to the machine-learned model 57. The machine-learned model 57 outputs the segmentation. Due to the training and architecture, the machine-learned model 57 operates to segment in a way differently than performed by a human.

The machine-learned model 57 is a neural network, support vector machine, or other machine-learning-based model. As a neural network, the machine-learned model 57 includes one or more blocks or layers having input channels for meta-data and imaging data. Within at least part of the network, the blocks or layers receive values for features related to the meta data and values for features related to the scan data. The blocks or layers maintain the separate channels for meta data and imaging data by having separate input channels and separate output channels for both. The blocks or layers may use information from one channel in the processing of the data in the other channel. The blocks or layers output values for features related to the meta data and output values for features related to the scan data.

In one embodiment, the block or layer with input and output couples of meta-data and imaging data includes normalization, linear, and non-linearity layers, portions, or operations. Additional, different, or fewer components forming the meta-data and imaging data paths in the block or layer may be used.

The display 58 is a CRT, LCD, projector, plasma, printer, tablet, smart phone or other now known or later developed display device. The display 58 displays the segmentation as a segmentation image. The segmentation image is displayed as part of, with, or separately from other MR images for the patient. The display 58 displays images for diagnosis, prognosis, and/or treatment planning. Due to the use of meta data and corresponding paths in the machine-learned model 57, the images may assist in diagnosis, prognosis, and/or treatment planning across a variety of scan settings and/or scanners.

The instructions, ground truths, meta-data, image data, machine-learned model, outputs, couples, inputs, segmentation, and/or other information are stored in a non-transitory computer readable memory, such as the memory 56. The memory 56 is an external storage device, RAM, ROM, database, and/or a local memory (e.g., solid state drive or hard drive). The same or different non-transitory computer readable media may be used for the instructions and other data. The memory 56 may be implemented using a database management system (DBMS) and residing on a memory, such as a hard disk, RAM, or removable media. Alternatively, the memory 56 is internal to the processor 54 (e.g. cache).

The instructions for implementing the processes, methods, and/or techniques discussed herein are provided on non-transitory computer-readable storage media or memories, such as a cache, buffer, RAM, removable media, hard drive or other computer readable storage media (e.g., the memory 56). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for segmentation of brain tissue in magnetic resonance imaging (MRI), the system comprising:
   an MRI scanner configured to scan the brain tissue of a patient, the scan providing scan data and meta data, the meta data representing the scan and the scan data representing the patient;
   an image processor configured to segment between different types of the brain tissue by application of the scan data and the meta data to a machine-learned model, the machine-learned model outputting the segmentation, wherein the machine-learned network comprises an input layer having a mixed block configured to receive the meta data and the scan data and output second meta information and second scan information;
   a display configured to display the segmentation of the brain tissue.

2. The system of claim 1 wherein the machine-learned model comprises a neural network with a first block having input channels for first features related to the meta data and for first features related to the scan data and having output channels for second features related to the meta data and for second features related to the scan data.

3. The system of claim 2 wherein the first block is configured to pass information from the first features related to the meta data to a path from the input of the first features related to the scan data to the output of the second features related to the scan data.

4. The system of claim 2 wherein the first block includes normalization, linear, and non-linearity layers.

5. The system of claim 1 wherein the scan data comprises image data and wherein the meta data comprises protocol data.

6. The system of claim 1 wherein the machine-learned network is configured to output the segmentation in response to input of both the scan data and the meta data.

7. The system of claim 1 wherein the machine-learned model is a neural network comprising layers including the input layer, wherein at least one of the layers includes image features separated by type of tissue.

8. The system of claim 1 wherein the machine-learned model is configured to receive input for different protocols used on different patients.

9. The system of claim 1 wherein the meta data is a magnetic resonance weighting type or a feature derived from the magnetic resonance weighting type.

10. The system of claim 1 wherein the meta data is a setting for a sequence parameter, geometrical information of a scan of the patient, task specific information and/or a feature derived from the setting, geometrical information, and/or task specific information as the protocol data.

11. The system of claim 1 wherein the machine-learned network comprises a U-net including the one or more additional mixed blocks at a U-net layer other than the input layer or an output layer of the U-net.

12. The system of claim 1 wherein the machine-learned network comprises a U-net with a conditional network including one or more additional mixed blocks, the conditional network outputting to a bottleneck of the U-net.

13. The system of claim 1 wherein the machine-learned network includes an instance normalization configured to output a skewness and/or kurtosis concatenated with the meta data.

14. The system of claim 1 wherein the machine-learned network was trained as a multi-task training using uncertainty estimation.

15. A system for segmentation of brain tissue in magnetic resonance imaging (MRI), the system comprising:
   an MRI scanner configured to scan the brain tissue of a patient, the scan providing scan data and meta data, the meta data representing the scan and the scan data representing the patient;
   an image processor configured to segment between different types of the brain tissue by application of the scan data and the meta data to a machine-learned model, the machine-learned model outputting the segmentation;
   a display configured to display the segmentation of the brain tissue;
   wherein the machine-learned network was trained with layers, one of the layers including the block and at least some of the other layers each having input couples and output couples, both the input couples and the output couples being a coupling of and relating to the scan data and the meta data.

16. A system for segmentation of brain tissue in magnetic resonance imaging (MRI), the system comprising:
   an MRI scanner configured to scan the brain tissue of a patient, the scan providing scan data and meta data, the meta data representing the scan and the scan data representing the patient;
   an image processor configured to segment between different types of the brain tissue by application of the scan data and the meta data to a machine-learned model, the machine-learned model outputting the segmentation;
   a display configured to display the segmentation of the brain tissue;
   wherein the machine-learned network comprises a mixed block configured to receive first protocol information as the meta data and first imaging information as the scan data and to output second protocol information and second imaging information, the mixed block comprising:
   a first normalization configured to output statistical information from the input imaging information to concatenate with the first protocol information and output normalized imaging information;
   a first fully connected layer configured to output a scale value to invert the normalized imaging information;
   a batch normalization receiving the concatenated first protocol information and the statistical information;
   a second fully connected layer configured to receive an output of the batch normalization and output to a summer and a first non-linear activation function;
   the first non-linear activation function configured to output the second protocol information;
   a multiplier configured to invert the normalized imaging information based on the scale value;
   a convolution layer configured to convolve with the inverted, normalized imaging information;
   the summer configured to sum an output of the convolution layer with the output of the second fully connected layer; and a second non-linear activation function configured to output the second imaging information in response to input of an output from the summer.

\* \* \* \* \*